(12) United States Patent
Wang et al.

(10) Patent No.: US 6,530,903 B2
(45) Date of Patent: Mar. 11, 2003

(54) SAFETY SYRINGE

(76) Inventors: Xiping Wang, No. 2, Suojiafen, Haidian District, Beijing City 100088 (CN); Bizhu Zhang, No. 1-7, Building 14, Capital Normal University, Beijing 100037 (CN); Xiaopeng Wang, Room 315, Building 6, P.B. 912, Beijing City 100083 (CN)

(*) Notice: Subject to any disclaimer, the term of this patent is extended or adjusted under 35 U.S.C. 154(b) by 2 days.

(21) Appl. No.: 09/789,669

(22) Filed: Feb. 22, 2001

(65) Prior Publication Data

US 2001/0021821 A1 Sep. 13, 2001

(30) Foreign Application Priority Data

Feb. 24, 2000 (CN) .......................................... 0020587 U

(51) Int. Cl.[7] ................................................ A61M 5/32
(52) U.S. Cl. ........................ 604/195; 604/110; 604/220
(58) Field of Search ................................. 604/220, 110, 604/195, 187, 111, 181, 192, 197, 198, 218, 228

(56) References Cited

U.S. PATENT DOCUMENTS

| 187,031 A | 2/1877 | McMorries |
| 2,617,359 A | 11/1952 | Van Horn et al. |
| 2,722,215 A | 11/1955 | Dahlgren |
| 2,880,723 A | 4/1959 | Adams |
| 3,306,290 A | 2/1967 | Weltman |
| 3,426,448 A | 2/1969 | Sarnoff |
| 3,848,593 A | 11/1974 | Baldwin |
| 3,889,673 A | 6/1975 | Dovey et al. |
| 3,890,971 A | 6/1975 | Leeson et al. |
| 4,026,287 A | 5/1977 | Haller |
| 4,034,755 A | 7/1977 | Schultz |
| 4,356,822 A | 11/1982 | Winstead-Hall |
| 4,425,120 A | 1/1984 | Sampson et al. |
| 4,507,117 A | 3/1985 | Vining et al. |
| 4,643,199 A | 2/1987 | Jennings, Jr. et al. |
| 4,643,200 A | 2/1987 | Jennings, Jr. |
| 4,664,654 A | 5/1987 | Strauss |
| 4,666,435 A | 5/1987 | Braginetz |
| 4,675,005 A | 6/1987 | DeLuccia |
| 4,692,156 A | 9/1987 | Haller |
| 4,710,170 A | 12/1987 | Haber et al. |
| 4,747,830 A | 5/1988 | Gloyer et al. |
| 4,790,822 A | 12/1988 | Haining |
| 4,804,370 A | 2/1989 | Haber et al. |
| 4,826,484 A | 5/1989 | Haber et al. |
| 4,838,870 A | 6/1989 | Haber et al. |

(List continued on next page.)

FOREIGN PATENT DOCUMENTS

| CN | 2270509 Y | 12/1997 |
| EP | 0347742 B1 | 12/1989 |
| EP | 0364387 A1 | 4/1990 |

(List continued on next page.)

Primary Examiner—Manuel Mendez
Assistant Examiner—Mark Han
(74) Attorney, Agent, or Firm—Rabin & Berdo, P.C.

(57) ABSTRACT

A safety syringe comprising a casing having a neck and a plunger having a distal portion, a weak portion, and a coupling portion covered by a hollow stopper having a membrane. The plunger is channeled in the casing and is moveable between an extended position and a compressed position. A needle holder, in the neck, contains a distally facing arrowhead and a proximally facing needle. Moving the plunger from an extended position to a compressed position, causes the arrowhead to puncture the membrane and engage the coupling portion. If the plunger is returned to the extended position, the needle is drawn into the casing and the distal portion of the plunger can be removed. If the plunger is re-compressed, the needle encounters a wall in the neck preventing the needle from exiting the casing. The syringe is easy to manufacture and prevents manufacturing burrs from being injected into patients.

19 Claims, 7 Drawing Sheets

U.S. PATENT DOCUMENTS

| | | |
|---|---|---|
| 4,887,999 A | 12/1989 | Alles |
| 4,892,107 A | 1/1990 | Haber |
| 4,894,055 A | 1/1990 | Sudnak |
| 4,898,589 A | 2/1990 | Dolgin et al. |
| 4,900,304 A | 2/1990 | Fujioka et al. |
| 4,900,307 A | 2/1990 | Kulli |
| 4,904,242 A | 2/1990 | Kulli |
| 4,906,231 A | 3/1990 | Young |
| 4,908,020 A | 3/1990 | Pettersen |
| 4,908,022 A | 3/1990 | Haber |
| 4,908,023 A | 3/1990 | Yuen |
| 4,909,794 A | 3/1990 | Haber et al. |
| 4,909,795 A | 3/1990 | Gelabert |
| 4,915,692 A | 4/1990 | Verlier |
| 4,915,700 A | 4/1990 | Noonan, Jr. |
| 4,919,652 A | 4/1990 | Alter et al. |
| 4,921,486 A | 5/1990 | DeChellis et al. |
| 4,923,443 A | 5/1990 | Greenwood et al. |
| 4,927,414 A | 5/1990 | Kulli |
| 4,929,231 A | 5/1990 | Pawlikowski |
| 4,931,040 A | 6/1990 | Haber et al. |
| 4,932,939 A | 6/1990 | Magre et al. |
| 4,932,940 A | 6/1990 | Walker et al. |
| 4,932,941 A | 6/1990 | Min et al. |
| 4,935,014 A | 6/1990 | Haber |
| 4,936,830 A | 6/1990 | Verlier |
| 4,941,879 A | 7/1990 | Butler et al. |
| 4,941,883 A | 7/1990 | Venturini |
| 4,944,723 A | 7/1990 | Haber et al. |
| 4,947,863 A | 8/1990 | Haber et al. |
| 4,950,240 A | 8/1990 | Greenwood et al. |
| 4,950,241 A | 8/1990 | Ranford |
| 4,950,243 A | 8/1990 | Estruch |
| 4,950,251 A | 8/1990 | Haining |
| 4,952,206 A | 8/1990 | Ibanez et al. |
| 4,955,869 A | 9/1990 | Bin |
| 4,955,870 A | 9/1990 | Ridderheim et al. |
| 4,957,490 A | 9/1990 | Byrne et al. |
| 4,961,728 A | 10/1990 | Kosinski |
| 4,966,593 A | 10/1990 | Lennox |
| 4,973,308 A | 11/1990 | Borras et al. |
| 4,973,309 A | 11/1990 | Sultan |
| 4,973,310 A | 11/1990 | Kosinski |
| 4,973,316 A | 11/1990 | Dysarz |
| 4,976,925 A | 12/1990 | Porcher et al. |
| 4,978,339 A | 12/1990 | Labouze et al. |
| 4,978,340 A | 12/1990 | Terrill et al. |
| 4,978,343 A | 12/1990 | Dysarz et al. |
| 4,979,943 A | 12/1990 | Trenner |
| 4,985,021 A | 1/1991 | Straw et al. |
| 4,986,812 A | 1/1991 | Perler |
| 4,986,813 A | 1/1991 | Blake, III et al. |
| 4,989,589 A | 2/1991 | Pekanmäki et al. |
| 4,994,034 A | 2/1991 | Botich et al. |
| 4,995,869 A | 2/1991 | McCarthy |
| 4,995,870 A | 2/1991 | Baskas |
| 4,995,874 A | 2/1991 | Strickland |
| 4,998,924 A | 3/1991 | Ranford |
| 5,000,735 A | 3/1991 | Whelan |
| 5,000,736 A | 3/1991 | Kaufhold, Jr. et al. |
| 5,000,737 A | 3/1991 | Free et al. |
| 5,004,460 A | 4/1991 | Gimeno |
| 5,007,903 A | 4/1991 | Ellard |
| 5,011,476 A | 4/1991 | Foster |
| 5,013,301 A | 5/1991 | Marotta, Jr. et al. |
| 5,017,187 A | 5/1991 | Sullivan |
| 5,019,043 A | 5/1991 | Segui Pastor et al. |
| 5,019,044 A | 5/1991 | Tsao |
| 5,019,045 A | 5/1991 | Lee |
| 5,019,046 A | 5/1991 | Kohler |
| 5,024,661 A | 6/1991 | Wender et al. |
| 5,026,346 A | 6/1991 | Spanner et al. |
| 5,026,354 A | 6/1991 | Kocses |
| 5,030,208 A | 7/1991 | Novacek et al. |
| 5,032,114 A | 7/1991 | Olovson |
| 5,034,002 A | 7/1991 | Duränzampa et al. |
| 5,037,393 A | 8/1991 | Ellgass |
| 5,037,394 A | 8/1991 | Mazurik et al. |
| 5,045,063 A | 9/1991 | Spielberg |
| 5,047,016 A | 9/1991 | Dolgin et al. |
| 5,047,017 A | 9/1991 | Koska |
| 5,049,133 A | 9/1991 | Vittan Pascual |
| 5,053,010 A | 10/1991 | McGary et al. |
| 5,059,179 A | 10/1991 | Quatrochi et al. |
| 5,059,180 A | 10/1991 | McLees |
| 5,059,181 A | 10/1991 | Agran |
| 5,061,249 A | 10/1991 | Campbell |
| 5,062,833 A | 11/1991 | Perler |
| 5,064,419 A | 11/1991 | Gaarde |
| 5,066,277 A | 11/1991 | Carrell et al. |
| 5,066,280 A | 11/1991 | Braithwaite |
| 5,066,281 A | 11/1991 | Stevenson-Michener |
| 5,067,490 A | 11/1991 | Haber |
| 5,067,942 A | 11/1991 | Jaffe et al. |
| 5,078,686 A | 1/1992 | Bates |
| 5,084,017 A | 1/1992 | Maffetone |
| 5,084,018 A | 1/1992 | Tsao |
| 5,084,019 A | 1/1992 | Gartz |
| 5,084,020 A | 1/1992 | Gartz |
| 5,085,638 A | 2/1992 | Farbstein et al. |
| 5,085,640 A | 2/1992 | Gibbs |
| 5,088,987 A | 2/1992 | Noonan, Jr. |
| 5,090,961 A | 2/1992 | Maruzik et al. |
| 5,090,962 A | 2/1992 | Landry, Jr. et al. |
| 5,092,853 A | 3/1992 | Couvertier, II |
| 5,098,382 A | 3/1992 | Haber et al. |
| 5,098,390 A | 3/1992 | Wallingford |
| 5,098,402 A | 3/1992 | Davis |
| 5,104,378 A | 4/1992 | Haber et al. |
| 5,106,371 A | 4/1992 | Zhao et al. |
| 5,106,372 A | 4/1992 | Ranford |
| 5,112,118 A | 5/1992 | Wiehle |
| 5,112,316 A | 5/1992 | Venturini |
| 5,114,404 A | 5/1992 | Paxton et al. |
| 5,114,405 A | 5/1992 | Winter |
| 5,114,410 A | 5/1992 | Caralt Batlle |
| 5,116,319 A | 5/1992 | van den Haak |
| 5,116,320 A | 5/1992 | Lo Duca |
| 5,120,309 A | 6/1992 | Watts |
| 5,120,310 A | 6/1992 | Shaw |
| 5,120,311 A | 6/1992 | Sagstetter et al. |
| 5,120,314 A | 6/1992 | Greenwood |
| 5,122,118 A | 6/1992 | Haber et al. |
| 5,122,124 A | 6/1992 | Novacek et al. |
| 5,125,898 A | 6/1992 | Kaufhold, Jr. et al. |
| 5,125,899 A | 6/1992 | Frignoli |
| 5,125,908 A | 6/1992 | Cohen |
| 5,127,906 A | 7/1992 | Landry, Jr. et al. |
| 5,135,495 A | 8/1992 | Arcusin |
| 5,147,303 A | 9/1992 | Martin |
| 5,149,323 A | 9/1992 | Colonna |
| 5,152,750 A | 10/1992 | Haining |
| 5,152,752 A | 10/1992 | Hammami |
| 5,152,753 A | 10/1992 | Hammami |
| 5,158,549 A | 10/1992 | McCarthy |
| 5,158,550 A | 10/1992 | Scholl, Jr. |
| 5,163,907 A | 11/1992 | Szuszkiewicz |
| 5,163,916 A | 11/1992 | Sunderland |
| 5,163,918 A | 11/1992 | Righi et al. |
| 5,167,641 A | 12/1992 | Schmitz |
| 5,171,300 A | 12/1992 | Blake, III et al. |
| 5,176,639 A | 1/1993 | Pozzi et al. |
| 5,176,640 A | 1/1993 | Nacci et al. |
| 5,180,369 A | 1/1993 | Dysarz |
| 5,180,370 A | 1/1993 | Gillespie |
| 5,181,912 A | 1/1993 | Hammett |
| 5,183,466 A | 2/1993 | Movern |
| 5,188,597 A | 2/1993 | Sweeney et al. |
| 5,188,599 A | 2/1993 | Botich et al. |
| 5,188,601 A | 2/1993 | King |

| | | | | | | |
|---|---|---|---|---|---|---|
| 5,188,614 A | 2/1993 | Hart | | 5,330,440 A | 7/1994 | Stanners et al. |
| 5,190,526 A | 3/1993 | Murray et al. | | 5,334,149 A | 8/1994 | Nortman et al. |
| 5,195,973 A | 3/1993 | Novick | | 5,334,155 A | 8/1994 | Sobel |
| 5,195,975 A | 3/1993 | Castagna | | 5,334,156 A | 8/1994 | Servano Gonzalez |
| 5,195,985 A | 3/1993 | Hall | | 5,334,158 A | 8/1994 | McLees |
| 5,201,708 A | 4/1993 | Martin | | 5,336,185 A | 8/1994 | Lynch et al. |
| 5,201,709 A | 4/1993 | Capra et al. | | 5,336,186 A | 8/1994 | Haber et al. |
| 5,201,710 A | 4/1993 | Caselli | | 5,336,187 A | 8/1994 | Terry et al. |
| 5,201,719 A | 4/1993 | Collins et al. | | 5,336,198 A | 8/1994 | Silver et al. |
| 5,205,823 A | 4/1993 | Zdeb | | 5,338,303 A | 8/1994 | King et al. |
| 5,205,824 A | 4/1993 | Mazur | | 5,338,304 A | 8/1994 | Adams |
| 5,205,825 A | 4/1993 | Allison et al. | | 5,338,310 A | 8/1994 | Lewandowski |
| 5,205,826 A | 4/1993 | Chen | | 5,338,311 A | 8/1994 | Mahurkar |
| 5,205,827 A | 4/1993 | Novacek et al. | | 5,342,308 A | 8/1994 | Boschetti |
| 5,207,646 A | 5/1993 | Brunel | | 5,342,309 A | 8/1994 | Hausser |
| 5,211,628 A | 5/1993 | Marshall | | 5,342,310 A | 8/1994 | Ueyama et al. |
| 5,211,629 A | 5/1993 | Pressly et al. | | 5,342,323 A | 8/1994 | Haining |
| 5,211,630 A | 5/1993 | Schmahmann | | 5,344,403 A | 9/1994 | Lee |
| 5,215,524 A | 6/1993 | Vallelunga et al. | | 5,344,405 A | 9/1994 | Richards |
| 5,215,533 A | 6/1993 | Robb | | 5,346,474 A | 9/1994 | King |
| 5,215,534 A | 6/1993 | De Harde et al. | | 5,346,475 A | 9/1994 | Gregorio |
| 5,219,333 A | 6/1993 | Sagstetter et al. | | 5,352,200 A | 10/1994 | Hammett et al. |
| 5,221,262 A | 6/1993 | Kite | | 5,352,202 A | 10/1994 | Hammett et al. |
| 5,222,942 A | 6/1993 | Bader | | 5,352,203 A | 10/1994 | Vallelunga et al. |
| 5,222,943 A | 6/1993 | Mazzara | | 5,360,404 A | 11/1994 | Novacek et al. |
| 5,222,944 A | 6/1993 | Harris | | 5,360,410 A | 11/1994 | Wacks |
| 5,222,945 A | 6/1993 | Basnight | | 5,364,359 A | 11/1994 | van den Haak |
| 5,226,881 A | 7/1993 | Pickhard | | 5,364,360 A | 11/1994 | Flumene et al. |
| 5,226,882 A | 7/1993 | Bates | | 5,368,568 A | 11/1994 | Pitts et al. |
| 5,226,884 A | 7/1993 | Murphy | | 5,370,619 A | 12/1994 | Rossi |
| 5,226,893 A | 7/1993 | Kayser | | 5,370,620 A | 12/1994 | Shonfeld |
| 5,232,447 A | 8/1993 | Schwarz et al. | | 5,370,654 A | 12/1994 | Abidin et al. |
| 5,232,458 A | 8/1993 | Chen | | 5,372,590 A | 12/1994 | Haber et al. |
| 5,242,400 A | 9/1993 | Blake, III et al. | | 5,374,250 A | 12/1994 | Dixon |
| 5,242,402 A | 9/1993 | Chen | | 5,376,000 A | 12/1994 | Petrussa |
| 5,250,030 A | 10/1993 | Corsich | | 5,376,080 A | 12/1994 | Petrussa |
| 5,254,093 A | 10/1993 | Bartlett et al. | | 5,378,240 A | 1/1995 | Curie et al. |
| 5,256,151 A | 10/1993 | Chul | | 5,395,346 A | 3/1995 | Maggioni |
| 5,257,976 A | 11/1993 | Fenet | | 5,401,246 A * | 3/1995 | Mazur et al. ............... 604/110 |
| 5,259,840 A | 11/1993 | Boris | | 5,403,337 A | 4/1995 | Platts |
| 5,259,841 A | 11/1993 | Hohendorf et al. | | 5,411,512 A | 5/1995 | Abidin et al. |
| 5,261,880 A | 11/1993 | Streck et al. | | 5,417,704 A | 5/1995 | Wonderley |
| 5,263,933 A | 11/1993 | Novacek et al. | | 5,423,843 A | 6/1995 | Werner |
| 5,263,934 A | 11/1993 | Haak | | 5,430,942 A | 7/1995 | Doucette |
| 5,263,942 A | 11/1993 | Smedley et al. | | 5,431,631 A | 7/1995 | Lu ............... 604/110 |
| 5,267,961 A | 12/1993 | Shaw | | 5,431,632 A | 7/1995 | Lu |
| 5,267,962 A | 12/1993 | Jenson | | 5,431,671 A | 7/1995 | Nallakrishman |
| 5,267,973 A | 12/1993 | Haber et al. | | 5,431,672 A | 7/1995 | Cote et al. |
| 5,269,760 A | 12/1993 | Bina | | 5,470,339 A | 11/1995 | Lerrick |
| 5,269,761 A | 12/1993 | Stehrenberger et al. | | 5,475,925 A | 12/1995 | Newman et al. |
| 5,273,538 A | 12/1993 | Chen | | 5,478,346 A | 12/1995 | Capewell |
| 5,273,539 A | 12/1993 | Chen | | 5,481,804 A | 1/1996 | Platts |
| 5,273,540 A | 12/1993 | Luther et al. | | 5,489,272 A | 2/1996 | Wirtz |
| 5,273,541 A | 12/1993 | Malenchek | | 5,496,340 A | 3/1996 | Abdidin et al. |
| 5,273,543 A | 12/1993 | Bell et al. | | 5,502,896 A | 4/1996 | Chen |
| 5,279,566 A | 1/1994 | Kline, Jr. et al. | | 5,507,762 A | 4/1996 | Abdidin et al. |
| 5,290,233 A | 3/1994 | Campbell | | 5,522,828 A | 6/1996 | Malilay |
| 5,290,235 A | 3/1994 | Polyblank et al. | | 5,527,329 A | 6/1996 | Gharibian |
| 5,295,973 A | 3/1994 | Chen | | 5,531,705 A | 7/1996 | Alter et al. |
| 5,304,137 A | 4/1994 | Fluke | | 5,531,754 A | 7/1996 | Shackelford, Sr. et al. |
| 5,304,138 A | 4/1994 | Mercado | | 5,533,975 A | 7/1996 | Lu |
| 5,304,150 A | 4/1994 | Duplan et al. | | 5,540,660 A | 7/1996 | Jenson |
| 5,306,258 A | 4/1994 | de la Fuente | | 5,545,175 A | 8/1996 | Abidin et al. |
| 5,308,329 A | 5/1994 | Mazur et al. | | 5,556,384 A | 9/1996 | da Encarnacão |
| 5,308,331 A | 5/1994 | Avila et al. | | 5,556,409 A | 9/1996 | Haining |
| 5,312,348 A | 5/1994 | Sans | | 5,562,623 A | 10/1996 | Shonfeld et al. |
| 5,312,372 A | 5/1994 | DeHarde et al. | | 5,562,624 A | 10/1996 | Righi et al. |
| 5,318,536 A | 6/1994 | Williams | | 5,562,626 A | 10/1996 | Sanpietro |
| 5,318,537 A | 6/1994 | Van Der Merwe | | 5,569,203 A | 10/1996 | Chen |
| 5,318,538 A | 6/1994 | Martin | | 5,569,211 A | 10/1996 | Lekhgolts et al. |
| 5,320,606 A | 6/1994 | Jore | | 5,569,281 A | 10/1996 | Abidin et al. |
| 5,324,265 A | 6/1994 | Murray et al. | | 5,569,282 A | 10/1996 | Werner |
| 5,328,473 A | 7/1994 | Fayngold et al. | | 5,571,127 A | 11/1996 | DeCampli |
| 5,328,475 A | 7/1994 | Chen | | 5,571,128 A | 11/1996 | Shapiro |
| 5,328,476 A | 7/1994 | Bidwell | | 5,572,968 A | 11/1996 | Esch et al. |
| 5,328,484 A | 7/1994 | Somers et al. | | 5,575,774 A | 11/1996 | Chen |

| | | |
|---|---|---|
| 5,578,015 A | 11/1996 | Robb |
| 5,599,351 A | 2/1997 | Haber et al. |
| 5,601,534 A | 2/1997 | Turner ............... 604/195 |
| 5,605,544 A | 2/1997 | Tsao |
| 5,607,402 A | 3/1997 | Dufresne et al. |
| 5,613,951 A | 3/1997 | Meyer et al. |
| 5,613,952 A | 3/1997 | Pressly, Sr. et al. |
| 5,620,454 A | 4/1997 | Pierce et al. |
| 5,624,408 A | 4/1997 | Helldin |
| 5,634,903 A | 6/1997 | Kurose et al. |
| 5,634,909 A | 6/1997 | Schmitz |
| 5,637,092 A | 6/1997 | Shaw |
| 5,656,031 A | 8/1997 | Thorne et al. |
| 5,658,257 A | 8/1997 | Ryles |
| 5,662,669 A | 9/1997 | Abidin et al. |
| 5,676,677 A | 10/1997 | Landis et al. |
| 5,681,292 A | 10/1997 | Tober et al. |
| 5,693,023 A | 12/1997 | Adams |
| 5,702,367 A | 12/1997 | Cover et al. |
| 5,722,960 A | 3/1998 | Duplan et al. |
| 5,725,501 A | 3/1998 | Lichtenberg |
| 5,730,751 A | 3/1998 | Dillon et al. |
| 5,733,261 A | 3/1998 | Obong |
| 5,749,886 A | 5/1998 | Abidin et al. |
| 5,759,177 A | 6/1998 | Whisson |
| 5,762,628 A | 6/1998 | Harper et al. |
| 5,769,822 A | 6/1998 | McGary et al. ............ 604/110 |
| 5,779,724 A | 7/1998 | Werner |
| 5,782,804 A | 7/1998 | McMahon |
| 5,785,687 A | 7/1998 | Saito |
| 5,788,677 A | 8/1998 | Botich et al. |
| 5,792,107 A | 8/1998 | Petrocelli |
| 5,792,162 A | 8/1998 | Jolly et al. |
| 5,797,880 A | 8/1998 | Erskine |
| 5,800,403 A | 9/1998 | Pressly, Sr. et al. |
| 5,810,782 A | 9/1998 | Saito |
| 5,814,017 A | 9/1998 | Kashmer |
| 5,820,605 A | 10/1998 | Zdeb et al. |
| 5,827,309 A | 10/1998 | Jolly et al. |
| 5,830,226 A | 11/1998 | Webb et al. |
| 5,843,107 A | 12/1998 | Landis et al. |
| 5,858,000 A | 1/1999 | Novacek et al. |
| 5,868,771 A | 2/1999 | Herbert et al. |
| 5,876,382 A | 3/1999 | Erickson |
| 5,882,342 A | 3/1999 | Cooper et al. |
| 5,885,256 A | 3/1999 | Chern et al. |
| 5,885,257 A | 3/1999 | Badger |
| 5,891,092 A | 4/1999 | Castellano |
| 5,891,105 A | 4/1999 | Mahurkar |
| 5,893,844 A | 4/1999 | Misawa |
| 5,893,845 A | 4/1999 | Newby et al. |
| 5,902,271 A | 5/1999 | Jentzen |
| 5,902,277 A | 5/1999 | Jentzen |
| 5,908,432 A | 6/1999 | Pan |
| 5,919,201 A | 7/1999 | Carter et al. |
| 5,921,960 A | 7/1999 | McGary et al. |
| 5,928,188 A | 7/1999 | McGary et al. |
| 5,935,104 A | 8/1999 | Janek et al. |
| 5,938,641 A | 8/1999 | Villanueva |
| 5,938,675 A | 8/1999 | Gharibian |
| 5,938,676 A | 8/1999 | Cohn et al. |
| 5,941,892 A | 8/1999 | Cohn et al. |
| 5,944,692 A | 8/1999 | McGary et al. |
| 5,968,019 A | 10/1999 | Lee |
| 5,968,020 A | 10/1999 | Saito |
| 5,971,964 A | 10/1999 | Donaldson |
| 5,976,111 A | 11/1999 | Hart |
| 5,980,487 A | 11/1999 | Jones et al. |
| 5,980,494 A | 11/1999 | Malenchek et al. ......... 604/198 |
| 5,984,898 A | 11/1999 | Garvin |
| 5,989,219 A | 11/1999 | Villas et al. |
| 5,993,417 A | 11/1999 | Yerfino et al. |
| 5,993,418 A | 11/1999 | Alexander |
| 5,993,419 A | 11/1999 | Lo et al. |
| 5,997,511 A | 12/1999 | Curie et al. |
| 5,998,898 A | 12/1999 | Fukutani et al. |
| 6,010,486 A | 1/2000 | Carter et al. |
| 6,013,056 A | 1/2000 | Pettersen |
| 6,013,059 A | 1/2000 | Jacob |
| 6,015,396 A | 1/2000 | Buttgen et al. |
| 6,015,419 A | 1/2000 | Strome et al. |
| 6,015,438 A | 1/2000 | Shaw |
| 6,017,325 A | 1/2000 | Yerfino et al. |
| 6,022,364 A | 2/2000 | Flumene et al. |
| 6,033,385 A | 3/2000 | Liu |
| 6,033,386 A | 3/2000 | Novacek et al. |
| 6,036,674 A | 3/2000 | Caizza et al. |
| 6,039,713 A | 3/2000 | Botich et al. ............... 604/110 |
| 6,048,354 A | 4/2000 | Lawrence |
| 6,050,974 A | 4/2000 | Allard et al. |
| 6,050,977 A | 4/2000 | Adams |
| 6,053,929 A | 4/2000 | Cohn et al. |
| 6,066,115 A | 5/2000 | Lai |
| 6,074,370 A | 6/2000 | Pressly, Sr. et al. |
| 6,077,244 A | 6/2000 | Botich et al. |
| 6,077,245 A | 6/2000 | Heinrich et al. |
| 6,080,461 A | 6/2000 | Wozniak et al. |
| 6,083,199 A | 7/2000 | Thorley et al. |
| 6,083,200 A | 7/2000 | Grimm et al. |
| 6,086,568 A | 7/2000 | Caizza |
| 6,090,077 A | 7/2000 | Shaw |
| 6,093,170 A | 7/2000 | Hsu et al. |
| 6,093,171 A | 7/2000 | Huang |
| 6,096,005 A | 8/2000 | Botich et al. |
| 6,099,500 A | 8/2000 | Dysarz |
| 6,102,893 A | 8/2000 | Aneas |
| 6,102,894 A | 8/2000 | Dysarz |
| 6,110,147 A | 8/2000 | Perouse |
| 6,113,617 A | 9/2000 | van der Merwe |
| 6,117,112 A | 9/2000 | Mahurkar |
| 6,117,113 A | 9/2000 | Novacek et al. |
| 6,120,479 A | 9/2000 | Campbell et al. |
| 6,123,688 A | 9/2000 | Botich et al. |
| 6,129,710 A | 10/2000 | Padgett et al. |
| 6,132,401 A | 10/2000 | Van Der Meyden et al. |
| 6,139,526 A | 10/2000 | Bedner et al. |

FOREIGN PATENT DOCUMENTS

| | | |
|---|---|---|
| EP | 0405039 A1 | 1/1991 |
| EP | 0438368 A1 | 7/1991 |
| EP | 0480862 A1 | 4/1992 |
| WO | WO89/00432 | 1/1989 |
| WO | WO89/09075 | 10/1989 |
| WO | WO91/14465 | 10/1991 |
| WO | WO92/09320 | 6/1992 |
| WO | WO92/11883 | 7/1992 |
| WO | WO92/18186 | 10/1992 |

* cited by examiner

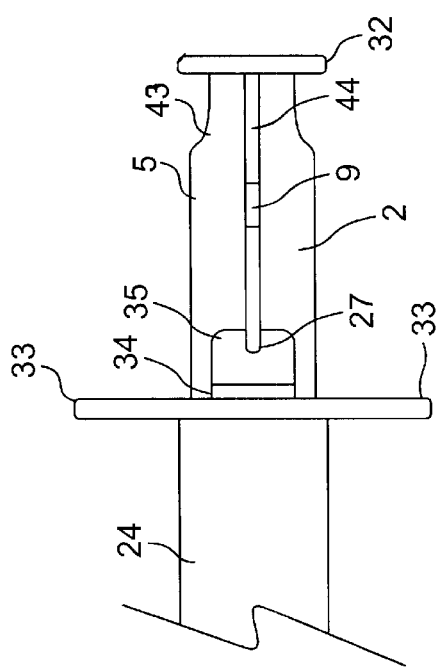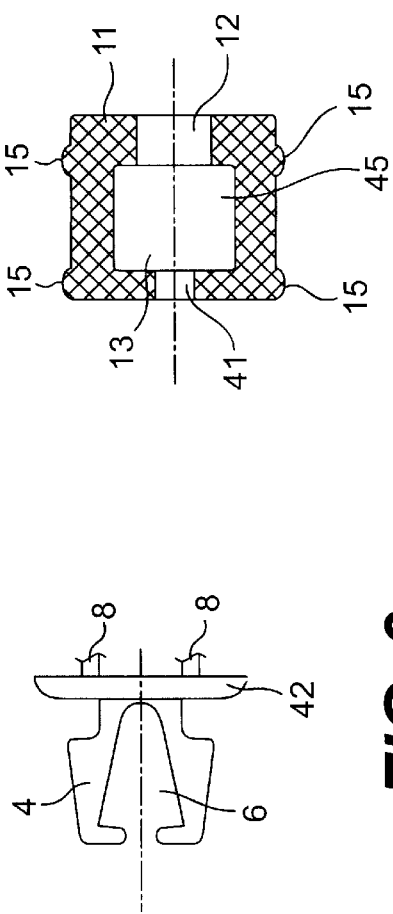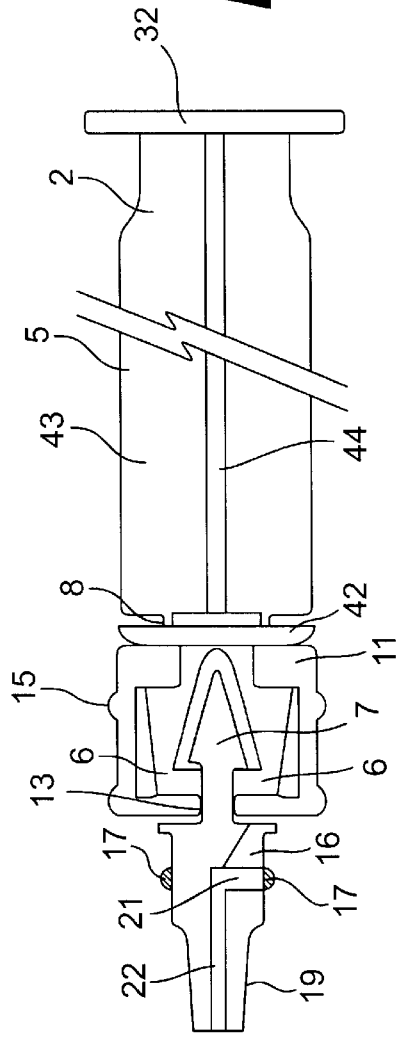

SAFETY SYRINGE

BACKGROUND OF THE INVENTION

This application claims priority to, and incorporates by reference, Chinese Patent Application No. 00205827.8 filed on Feb. 24, 2000.

1. Field of the Invention

The present invention relates to a syringe, particularly, to a safety syringe, belonging to the medical device technical field. Safety syringes are designed for one-time use and are, therefore, not re-useable.

2. Background of the Art

In the medical field, there is a great need to avoid cross-contamination or infection which may be caused when a syringe is used more than once. Single use syringes have long been thought as being one way to avoid these potential problems. However, current single use syringes present a variety of problems. Some syringes which claim to be "single use" in actuality can be reused with user intervention. Some syringes are designated as "single use" solely because they are to be discarded after use pursuant to a regulation; nothing prevents their reuse. Some syringe designs expose the drug or bodily fluid contained therein to reactive components of the syringe (e.g. a spring used to retract the plunger). In addition, some syringes, although not capable of being reused, present health risks to the medical personnel handling them. Accordingly, there is a need for a single use syringe which is: (a) easy to use; (b) incapable of being reused; (c) presents little or no danger to medical personnel after use; (d) designed in such a way as to prevent contact between reactive syringe components and the fluid contained within the syringe; and (e) capable of being manufactured at low cost.

Currently, there are mainly two classes of safety syringes. One class of syringes, which employs a spring to retract a needle into the syringe, is represented in U.S. Pat. Nos. 5,769,822, 5,980,494, and 6,039,713. Although these syringes are effective and easy to use, the also have inherent disadvantages. First, the spring-loaded structure is complicated because of the number of parts involved creates difficulties in constructing the syringe. Second, due to the complicated structure, the costs of manufacturing are high making marketing difficult. Third, due to the location of the spring at the needle end of the syringe, it is difficult to position the fluid close to the inlet to the needle; this increases fluid residue and makes removal of air bubbles more difficult.

The second class of syringes employs a locking mechanism on the plunger which engages a corresponding structure at the base of the needle when the plunger is completely compressed. A subsequent withdrawal of the plunger pulls the needle into the syringe barrel. The structure of these syringes is simpler and the cost of production lower in comparison to the former class. However, this class of syringes also has disadvantages. For example, in Chinese Patent CN2270509Y, the corresponding parts of the locking mechanism between the needle and the plunger are exposed to fluid contained within the syringe. Accordingly, any burrs on the parts which result from manufacturing may fall into the fluid and be thereafter accidentally transmitted to the patient giving rise to a potentially dangerous situation. In addition, in many of these syringes, the locking mechanism can be disengaged and the syringe reused.

U.S. Pat. No. 5,601,534 discloses a one-time-use safety syringe comprising a simple structure which reliably releases gases and retains a very small amount of residual fluid. However, it also presents disadvantages. The structure employs an inward facing needle extension which is bent by an arrowhead attached to the plunger. The extension is bent into a cavity in the plunger such that when the plunger is pulled away from the needle, the needle is pulled into the syringe barrel.

A first disadvantage is that the size of the extension must correspond to the size of the needle; a large needle requires a large extension which is not as easily bent thereby degrading the integrity of the engagement with the plunger.

A second disadvantage is that the rubber stopper, which houses the cavity, is solid. Due to the solid nature of the stopper, the extension must completely pierce the stopper to create a strong engagement with the cavity. To create this strong engagement requires a strong compression of the plunger at the completion of the injection; this can be difficult when the needle and needle extension are large.

A third disadvantage results with large needles. A large compressive force needs to be applied to the plunger to complete an injection with a large needle. This force counteracts the force necessary for the needle extension to puncture the plunger. To address this problem, the needle's engagement with the barrel head needs to enhanced. However, by enhancing the needle's engagement with the barrel head, it becomes more difficult to withdraw the needle into the syringe barrel after the injection is complete.

Fourth, the engagement of the needle extension and the plunger is such that upon withdrawal of the needle into the syringe barrel, residual fluid in the barrel can leak out of the syringe.

Fifth, the size of the plunger cavity corresponds to the size of the needle. Accordingly, one plunger can not be used with a variety of needle sizes. Therefore, medical personnel must maintain an inventory of various sizes of plungers which is costly and which occupies precious storage space.

SUMMARY

A solution to the aforementioned deficiencies in the art are resolved by the safety syringe herein described. Specifically, the presently described syringe has the following advantages over the prior art: (a) the hooks within the stopper which engage the arrowhead are not in contact with the fluid contained in the syringe thereby reducing the potential for manufacturing burrs to fall into the fluid and thereby be injected into the patient. The structure is possible because the engagement of the needle holder and the plunger occurs when the arrowhead pierces the stopper membrane. After the completion of the injection thereby establishing this engagement, the syringe can not be reused. Moreover, the puncturing of the membrane requires a force which is much smaller than the force necessary to compromise the o-ring seal in the plunger neck; accordingly the counteractive force problems in the prior art are eliminated; (b) the o-ring positioned in the syringe neck prevents fluid from escaping when the needle is initially pulled toward the syringe barrel; (c) the syringe has a simple structure which is both easy to use and manufacture; (d) the cavity in the stopper and the arrowhead can be used with any size needle (i.e. the size of the cavity and the arrowhead is not dependent on the size of the needle); and (e) the size of the needle does not compromise the integrity of the locking between the plunger and the needle holder.

These and other advantages are made possible by a safety syringe comprising a syringe casing having a distal end and a proximal end. A plunger is channeled in the syringe casing and is capable of moving from an extended position to a compressed position. The plunger has a weak portion, a distal portion, and a coupling portion. A stopper, having a membrane, is affixed to the coupling portion of the plunger; the membrane is between the proximal end of the syringe casing and the plunger. A needle holder, initially coupled to the proximal end of the syringe casing, has a distally facing arrowhead and a proximally facing needle. When the plunger is moved from the extended position to the compressed position, the arrowhead punctures the membrane and lockingly engages the coupling portion of the plunger. Subsequently, when the plunger is returned to the extended position, the needle holder and needle are drawn into an interior of the syringe casing.

In the safety syringe above-described, the weak part of the plunger may include a plurality of tines. In this situation, when the plunger is returned to the extended position from the compressed position, the distal portion of the plunger may be disengaged from the weak portion by breaking the tines.

In a preferred embodiment, the safety syringe includes a plurality of o-rings formed on an outer surface of the stopper. The plurality of o-rings frictionally engage an inner surface of the syringe casing when the plunger is moved between the extended position and the compressed position.

In the safety-syringe above-described, the proximal end of the syringe casing comprises a cylindrical neck portion which houses the needle holder. The cylindrical neck portion comprises a circumferential channel formed on an inner surface thereof. The needle holder comprises a circumferential o-ring on an outer surface thereof which is sized to substantially fill the channel.

The safety-syringe may also include a safety mechanism. The safety mechanism comprises a check plate which is affixed to an outer surface of the syringe casing and which is adapted to move from an unlocked position to a locked position. The check plate is designed to engage a notch in a side of the distal portion of the plunger. When the check plate is in the locked position, it engages the notch thereby preventing the plunger from moving from the extended position to the compressed position.

In the presently described safety syringe, the needle and the syringe casing have longitudinal axes. Before engagement of the arrowhead and the coupling portion, the needle axis and the syringe casing axis are substantially parallel. By way of contrast, after the needle holder and the needle are drawn into the interior of the syringe casing, a mechanism alters the orientation of the needle axis with respect to the syringe axis so that they are not substantially parallel. Additionally, the proximal end of the syringe casing comprises a cylindrical neck portion which houses the needle holder; a circumferential wall extends from an interior end of the cylindrical neck portion to an outer surface of the proximal end of syringe casing. Due to the misalignment of the needle axis and the syringe casing axis, the needle will contact the wall if the plunger is moved toward the compressed position.

Ideally, the stopper substantially covers the coupling portion of the plunger when the plunger is in the extended position. Moreover, when the plunger is in the compressed position (i.e., after engagement of the arrowhead and the coupling portion housed within the stopper), the stopper substantially covers the arrowhead and the coupling portion.

A second embodiment of a safety syringe includes a syringe barrel and a needle holder, having an arrowhead at a rear portion thereof, sealingly installed onto a front end of the syringe barrel. The arrowhead has a circumferential groove disposed at its base. A needle is sleeved onto the needle holder. A cylindrical rubber stopper, coupled to a plunger, has a membrane at on one end and a bore at the other end. The plunger has an coupling portion dimensioned to engage the arrowhead. The rubber stopper is hollow and is sleeved over the plunger coupling portion. Moreover, the plunger is moveable between an extended position and an compressed position at which an injection is completed. The rubber stopper and the plunger are sequentially installed into the syringe barrel.

In the syringe of this type, the membrane end of the rubber stopper faces the arrowhead; at the completion of the injection, the arrowhead pierces the membrane and engages the coupling portion. After this engagement, when the plunger is drawn backwards towards the extended position, the needle holder and the needle are drawn into the syringe barrel.

Preferably, the syringe also includes an inner sealing channel on an internal side of the front end of the syringe barrel. Correspondingly, a sealing ring sleeved onto the needle holder is preferably dimensioned to match the inner sealing channel. A rear portion of the inner sealing channel should have a smaller arc than an arc of the sealing ring. Moreover, a frontal portion of the inner sealing channel should have an inclined face having an arc larger than the arc of the rear portion. In a syringe having these channel characteristics, the needle holder can be slideably engaged in the front end of the syringe barrel by means of the sealing ring and can be moved in the direction of the syringe barrel when the plunger is withdrawn are engagement of the arrowhead and coupling portion.

The plunger in a safety syringe of this nature preferably comprises a weak portion and a resistance plate fixedly connected to the coupling portion. Moreover, the plunger preferably has a "+" shaped formed by a vertical rib plate and a horizontal cross rib plate. The vertical rib plate is weakly connected to the resistance plate by means of a plurality of tines. After completion of the injection and after the needle holder and needle are drawn into the syringe barrel, the tines of the weak portion can be broken upon application of a bending moment.

Similar to the first embodiment, the safety syringe may also include a mechanism by which premature use of the syringe is prevented. Specifically, the syringe may include a safety mechanism having a wing plate, a check plate, and a flexible film connecting the wing plate and the check plate. The safety mechanism is positioned on an exterior surface of the syringe barrel at a position proximate to an insertion bore into which the plunger is inserted. The check plate and one rib of the vertical rib plate have corresponding grooves which may be engaged if the check plate is rotated toward the vertical rib plate by means of the flexible film. If the grooves of the check plate and the vertical rib plate are engaged, premature completion of the injection is prevented.

Ideally, a plane forming the base of the arrowhead is not perpendicular to a central axis of the syringe barrel. In this fashion, after the needle is drawn into the syringe barrel, the axis of the needle will be directed toward an inner wall of the syringe barrel; a subsequent re-compression of the plunger toward the compressed position will cause the needle to abut the inner wall of the syringe barrel.

The present invention also contemplates a method for preventing reuse of a syringe. The method uses a syringe having a syringe casing which, in turn, has a longitudinal axis, a distal end, and a proximal end having a cylindrical neck portion. In the syringe used by the method, a circumferential wall extends from an interior end of the cylindrical neck portion to an outer surface of the proximal end of syringe casing. A plunger having a weak portion, a distal portion, and a coupling portion, is channeled in the syringe casing and is moveable from an extended position to a compressed position. A stopper having a membrane is affixed to the coupling portion of the plunger; the membrane is between the proximal end of the syringe casing and the plunger. A needle holder, housed in the cylindrical neck portion of the syringe casing, has a distally facing arrowhead and a proximally facing needle having an axis and a needle tip.

The method includes: (I) moving the plunger from the extended position to the compressed position; (II) puncturing the membrane with the arrowhead when the plunger is in the compressed position; (III) coupling the arrowhead to the coupling portion; (IV) returning the plunger to the extended position and thereby drawing the needle holder and the needle into an interior of the syringe casing; and (V) preventing reuse of the needle by either (a) altering the orientation of the needle axis with respect to the syringe casing axis from an orientation in which the axes were substantially parallel to an orientation in which the needle tip will encounter the circumferential wall if the plunger is moved back toward the compressed position or (b) disengaging the distal portion of the plunger by breaking the weak part.

In the method in which the preventing reuse of the needle is preformed by altering the orientation of the needle axis with respect to the syringe casing, a further step is possible. This method may also include bending the needle when the needle tip encounters the circumferential wall when the plunger is subsequently moved toward the compressed position.

In addition, in the method in which the preventing reuse of the needle is performed by disengaging the distal portion of the plunger from the weak part, the disengagement may occur if the weak part of the plunger is comprised of a plurality of tines which are easily broken upon application of a bending moment applied to the plunger when the plunger is in the extended position.

BRIEF DESCRIPTION OF THE DRAWINGS

The accompanying figures, which are incorporated in and constitute a part of the specification, illustrate presently preferred embodiments of the invention. Together with the above general description and the following detailed description, the figures serve to explain the principles of the invention.

FIG. 9 is a side view of the weak part of the plunger of FIG. 8 showing only the needle end portion attached to the weak part;

FIG. 10 is a cross-sectional view of a stopper into which the needle portion of the stopper is inserted;

FIG. 11 is a cross sectional side view showing the engagement of the plunger and the needle holder; and FIG. 12 is a top end view of the syringe casing showing the locking mechanism and finger supports.

DETAILED DESCRIPTION

Figure 1:
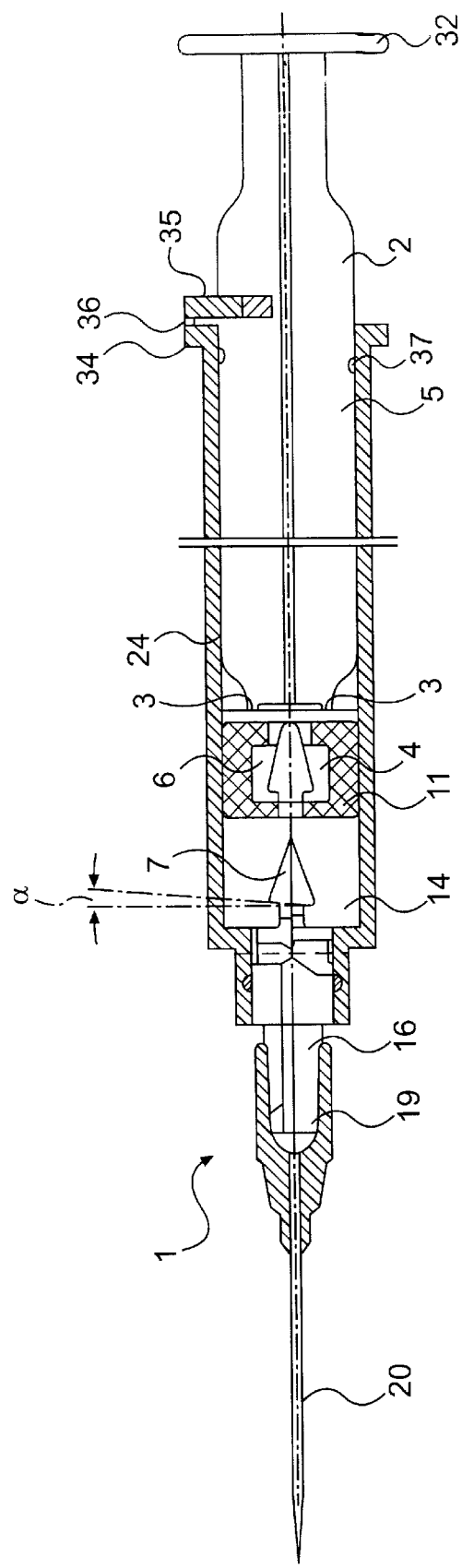
FIG. 1 is a cross sectional side view of a syringe showing the syringe prior to complete compression of the plunger and where a locking mechanism, in a locked position, prevents such compression.

A preferred embodiment of a safety syringe 1 will be hereafter described with reference to the figures. FIG. 1 shows a non-activated safety syringe 1 comprising a plunger 2 having a weak part 3, a coupling portion 4, and a distal portion 5. The plunger sits within a syringe casing 24. Attached to the coupling portion 4 of the plunger 2 is a stopper 11. The area within the casing 24 between a needle holder 16 and the stopper 11 defines a fluid chamber 14 which contains a fluid to be administered to a patient.

Figure 6:
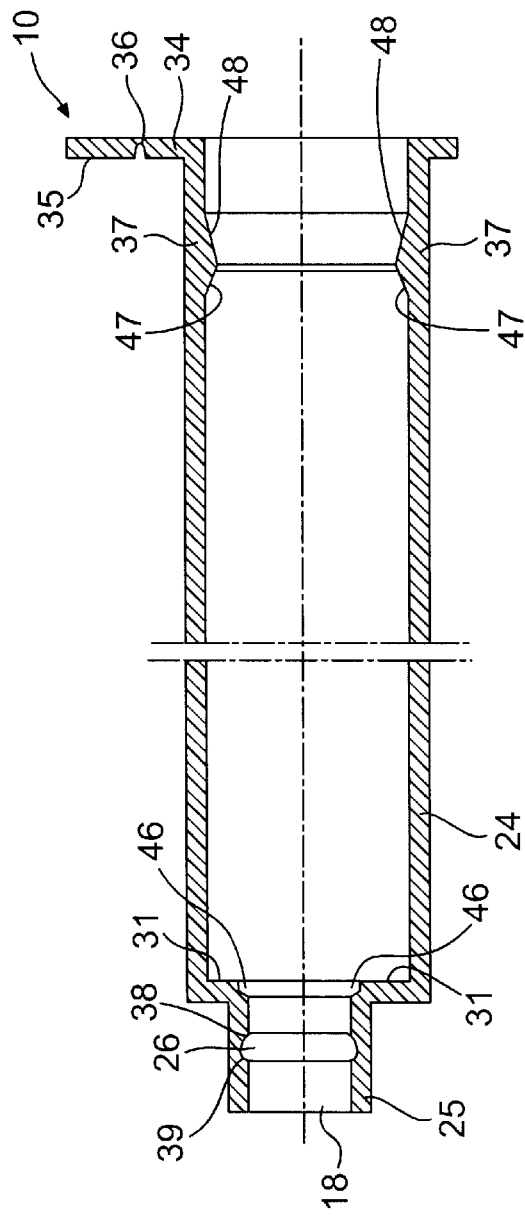
FIG. 6 is a cross sectional side view of a syringe casing.
Figure 7:
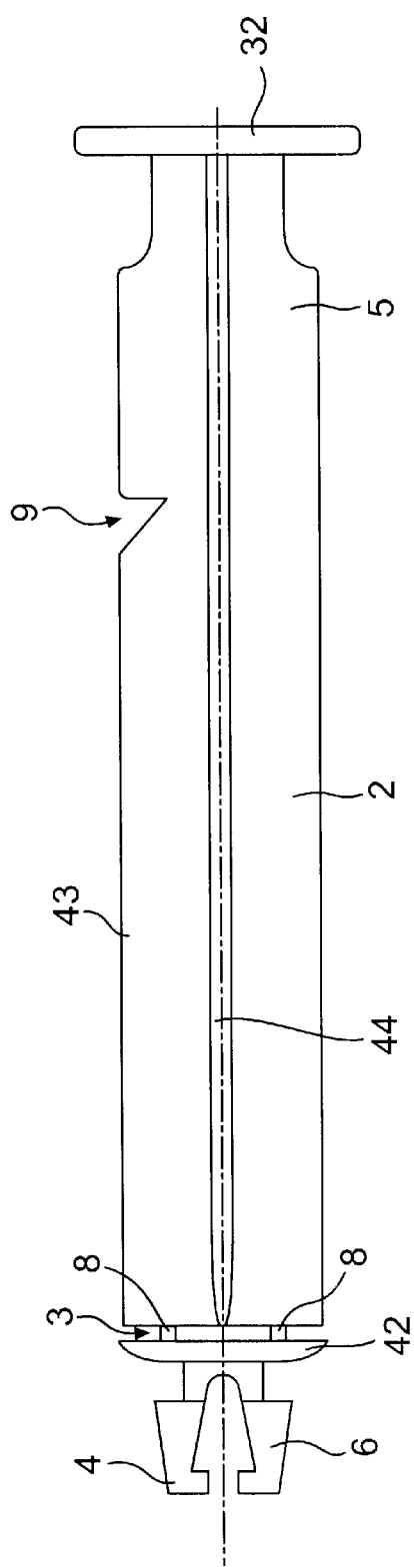
FIG. 7 is a side view of a plunger.
Figure 8:
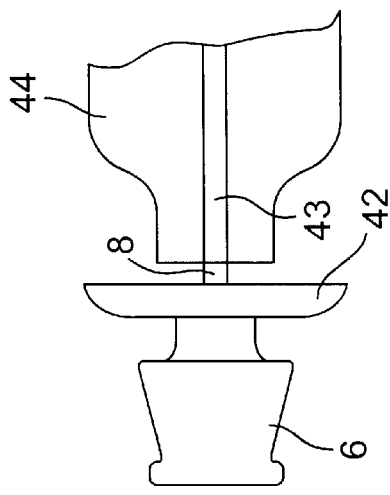
FIG. 8 is a side view of a weak part of a plunger at which the plunger may be broken after the syringe is used showing the needle end and the pushing end portions of the plunger attached at the weak part.

FIG. 7 shows a side view of the plunger 2 whereas FIG. 8 focuses on the weak part 3 of the plunger 2. On either side of the weak part 3 are the coupling portion 4 and the distal portion 5. The coupling portion 4 has a front resistance plate 42. The resistance plate 42 has a transitional arc brim on its front face whereas its rear face is substantially flat. The outer diameter of the resistance plate 42 is equal to or slightly smaller than the inner diameter of the syringe casing 24. Although the diameter of the resistance plate 42 can be 0.1 mm smaller than the inner diameter of the syringe casing 24, it should be larger than the inner diameter of a resistance ring 37 (hereafter described) circumferentially formed on the inner surface of the syringe casing 24 (as shown in FIG. 6). Preferably, the weak part 3 is comprised of a small number of tines 8 which are attached to and positioned between the front resistance plate 42 and the distal portion 5. The tines 8 are designed to break easily when a bending moment is applied to the distal portion 5 when the plunger 2 is in a fully extended position. However, numerous other embodiments can be employed to create a breakable weak part 3.

The coupling portion 4 contains a plurality of hooks 6 which are designed to engage an arrowhead 7, as described below. The distal portion 5, on the other hand, can have a variety of cross sections. To balance cost and effectiveness, a "+" shape is preferable for the distal portion 5; if this configuration is used, it is preferable to have a flat plate 32 affixed to the end of the plunger 2 so that a user will have a broad flat surface on which to place a thumb when compressing the plunger 2 into the syringe casing 24. If the "+" shape is employed to form the distal portion 5, one plane of the distal portion 5 (i.e. a vertical rib plate 43) may have tines 8 extend therefrom (and attach to the front resistance plate 43) whereas the other plane of the "+" shaped distal portion 5 (i.e. a horizontal rib plate 44) may have no such tines 8. Moreover, if the "+" shape is employed, in one of the sides of the cross section, a notch 9 may be positioned. The notch 9 is designed to engage a safety mechanism 10 which is preferably attached to the syringe casing 24, as described below.

As can be seen in FIG. 10, centrally positioned in one end of a stopper 11 is a bore 12 which leads to a cavity 45. The bore 12 does not completely penetrate the stopper 11.

Rather, the other end of the stopper 11 comprises a membrane 13, the function of which is hereafter described. However, the bore 12 is extended by a smaller diameter bore 41 which extends to an inner side of the membrane 13. In construction, the coupling portion 4 of the plunger 2 is completely inserted into the bore 12 of the stopper 11 until it rests in the cavity 45. Preferably, the stopper 11 is made of rubber or a rubber-like material which allows the stopper to prevent the fluid (to be administered to a patient) from escaping a fluid chamber 14 in the syringe 1. In preventing the passage of such fluids, the stopper 11 has a plurality of o-rings 15 formed along its outer circumference which frictionally engage the inner surface of the fluid chamber 14. The stopper 11 substantially covers the hooks 6 of the coupling portion 4 of the plunger 2; the hooks 6 are positioned in the cavity 45 and are covered by the membrane 13 prior to an activation of the syringe described below.

Figure 5:
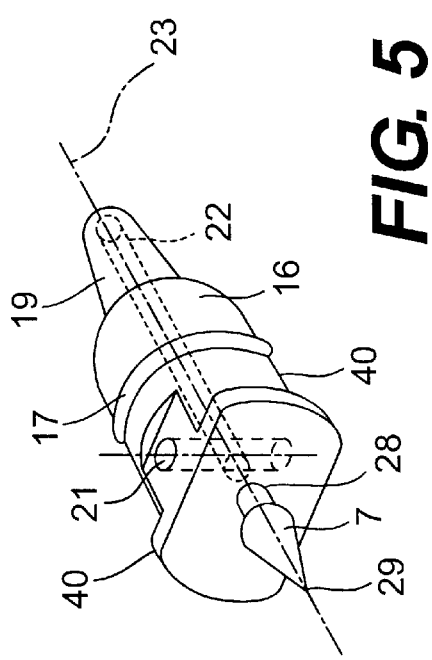
FIG. 5 is a perspective view of the needle holder.

FIG. 5, which shows a perspective view of a needle holder 16, depicts another o-ring 17 in a central portion of the needle holder 16. The o-ring 17 of the needle holder 16 sits within a circumferential channel and prevents the fluid (to be administered to a patient) from escaping the syringe 1 through a bore 18, described below, and also prevents accidental needle ejection when large compressive loads are applied to the plunger 2. The o-ring 17 is designed to engage a circumferential channel 26 in the cylindrical neck portion 25 of the syringe casing 24, (as shown in FIG. 2) as hereafter described.

On one side of the o-ring 17 is a needle adapter 19 onto which a needle 20 is fixed. The needle adapter 19 is conical in shape which allows needles of various sizes to be fixed on the needle holder 16. On the other side of the o-ring 17 is an arrowhead 7. On one end of the arrowhead is a point 29. At the base of the arrowhead 7 is a circumferential groove 28 designed to engage the hooks 6 of the plunger 2, as described below. The base of the arrowhead 7 is made to be inclined, i.e. the angle of the base is at an angle a with respect to a coplanar line which is perpendicular to the axis of the syringe casing 24; the angle is preferably approximately 5 degrees. This angular orientation allows the needle holder 16 to be oriented at an angle when it is withdrawn into the syringe casing 24, as described below.

Figure 2:
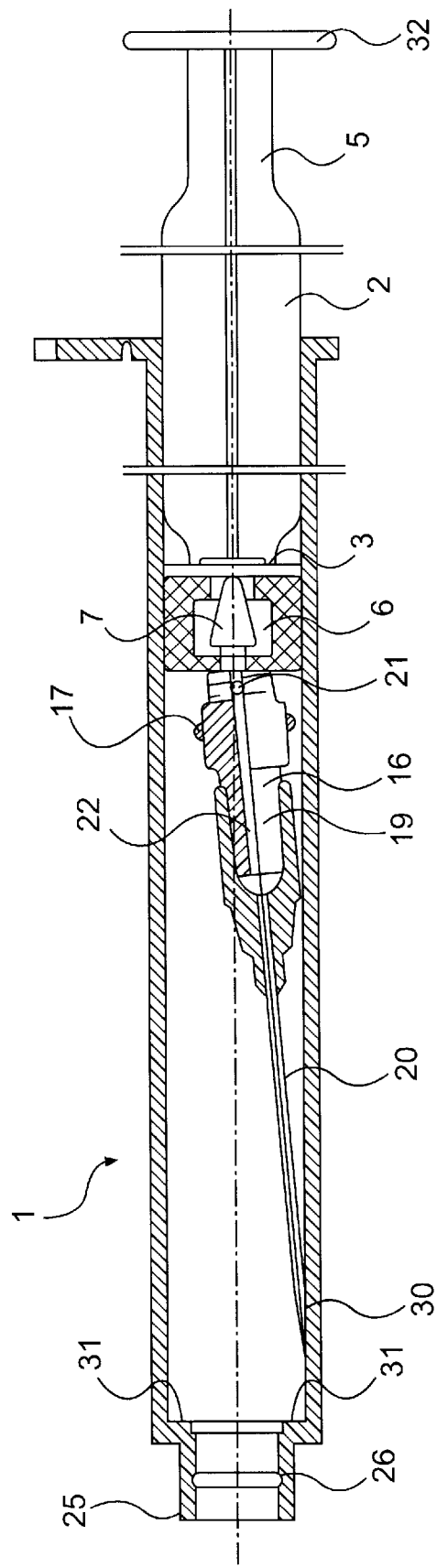
FIG. 2 is a cross sectional side view of a syringe showing the needle drawn into the chamber after the syringe's one-time use.

At the base of the groove 28 there are two flaps 40 which are designed to engage the wall 31 (as shown in FIG. 2) in the cylindrical neck 25 when the needle holder 16 is positioned in the cylindrical neck 25. By engaging the wall 31, the flaps 40 prevent the needle holder 16 from being ejected when the plunger 2 is compressed. Moreover, the engagement of the flaps 40 and the wall 31 reduces injection residue.

A needle holder axis 23 is defined by a line passing through the arrowhead 7 in the direction of the needle adapter 19. Positioned in the needle adapter 19 of the needle holder 16 is a bore 22 which travels from the needle adapter end of the needle holder 16 along the axis 23 to a position on needle holder 16 which is on the arrowhead 7 side of the o-ring 17; the bore 22 does not extend into the arrowhead 7. A trans-bore 21 is perpendicularly drilled through the needle holder 16 at the end of the bore 22, i.e. perpendicular to the axis 23 of the needle holder 16. The two bores 21 and 22 thereby form a "T" shaped channel in the needle holder 16. When a needle 20 is attached to the needle adapter 19 the "T" shaped channel extends into the needle. This construction allows a fluid, housed within the fluid chamber 14, to pass through the "T" shaped channel (when the plunger 2 is depressed), through the needle 20, and into a patient.

FIG. 6 shows a cross sectional side view of the syringe casing 24. The casing 24 is substantially cylindrical and hollow. On one end of the casing 24, there is a narrower cylinder 25 which extends from the casing 24. Prior to use, the cylinder 25 (which comprises bore 18) holds the needle holder 16 with the arrowhead 7 distally extending into the fluid chamber 14. In the cylinder 25, there is a circumferential channel 26 on the inner surface of the cylinder 25. O-ring 17 of the needle holder 16 initially rests within channel 26 and thereby prevents drugs, stored in the fluid chamber 14, from being able to leak out of the syringe 1. The circumferential channel 26 has an asymmetric cross-section; the rear portion 38 has the same arc as the o-ring 17 whereas the frontal portion 39 (i.e. the portion closest to the needle end of the syringe 1) has a larger arc.

Attached to the other end of the casing 24 are two finger supports 33 (as shown in FIG. 12) and the safety mechanism 10. Safety mechanism 10 is formed onto the casing in such a way as to allow it to swing toward and away from the plunger 2 when the plunger 2 is positioned within the casing 24. To allow the safety mechanism 10 to swing, the safety mechanism is comprised of a wing plate 34 (which is a part of the finger support 33) which is connected to a check plate 35 by means of a thin plastic film 36. Preferably, the check plate 35 has a notch 27 (as shown in FIG. 12) which is sized to correspond to the thickness of one of the sides of the "+" shaped plunger. When the check plate 35 is rotated from an unlocked position and toward the plunger 2 and thereby into a locked position, the notch 27 of the check plate 35 may engage the notch 9 in one of the sides of the "+" shaped plunger 2. A user will be unable to activate (as described below) the syringe 1 by depressing the plunger 2 while the notch 27 is engaged with notch 9 as this engagement prevents further compression of the plunger 2; accordingly, completely activation of the syringe 1 is avoided.

In addition, the rear end of the syringe casing 24 also comprises a resistance ring 37 formed on the interior of the casing 24 near the rear end of the casing 24 in which the plunger is inserted. The resistance ring 37 has a cross-section substantially triangular in shape. The cross-section of the ring 37 is such that the portion 47 of the cross-section facing the needle end of the syringe 1 is steeper than the portion 48 facing the plunger 2 end of the syringe 1. In this fashion, the portion 47 of the ring 37 facing the needle 20 end of the syringe 1 has a larger axial angle with respect to the axis of the syringe casing 24; the angle is preferably about 60 degrees. The side of the ring 37 facing the plunger 2 end of the syringe 1 has a smaller axial angle with respect to the axis of the syringe casing 24; the angle is preferably about 10 degrees.

During assembly, the needle holder 16 is channeled into the syringe casing 24 through the plunger 2 end of the casing 24. The needle holder 16 is then pushed forward until the o-ring 17 snaps into the circumferential channel 26 and the flaps 40 hit a circumferential rim 46 located in the cylindrical neck portion 25 adjacent the circumferential wall 31. The hooks 6 of the plunger 2 are inserted into the bore 12 in the stopper 11 until the are housed in the cavity 45; the combination of the plunger 2 and the stopper 11 is then inserted into the syringe casing 24. In so doing, the front resistance plate 42 of the plunger 2 rides over the resistance ring 37 to become permanently housed with the syringe casing 24. The check plate 35 of the safety mechanism 10 should be turned down toward the plunger 2 (i.e. into the locked position) by means of the bendable film plastic film 36 and its notch 27 should be aligned with the side of the "+" shaped plunger containing the corresponding notch 9 so that an engagement of the notches 9, 27 can occur thereby preventing complete compression of the plunger 2 in the syringe casing 24.

Activation of the syringe 1 occurs as follows. When the safety mechanism 10 is not engaged with one of the sides of the plunger 2 and a user depresses the plunger 2 to compress the fluid chamber 14, drugs in the fluid chamber are forced into the "T" shaped channel of the needle holder 16 and into (and out of) the needle 20. As the plunger is compressed, the membrane 13 of the stopper 11 approaches the arrowhead 7. With continued compression, the point 29 of the arrowhead 7 pierces the membrane 13 causing the arrowhead 7 to pass through bore 41 and into cavity 45 in which the arrowhead 7 engages the hooks 6. Again, with continued compression, the arrowhead 7 radially separates the hooks 6 to a point at which the hooks 6 snap into the circumferential groove 28 around the base of the arrowhead 7 as shown in FIG. 11. In this fashion the arrowhead 7 and the plunger 2 become permanently engaged within the stopper 11. Due to the engagement of the hooks 6 with the circumferential groove 28, when a user pulls on the plunger 2, the needle holder 16 (to which the arrowhead 7 is attached) and the needle 20 are pulled into the syringe casing 24. The user is unable to pull the plunger (with needle attached) out of the syringe casing 24 because front resistance plate 42 of the plunger 2 engages the frontal portion 47 of the resistance ring 37.

Figure 4:
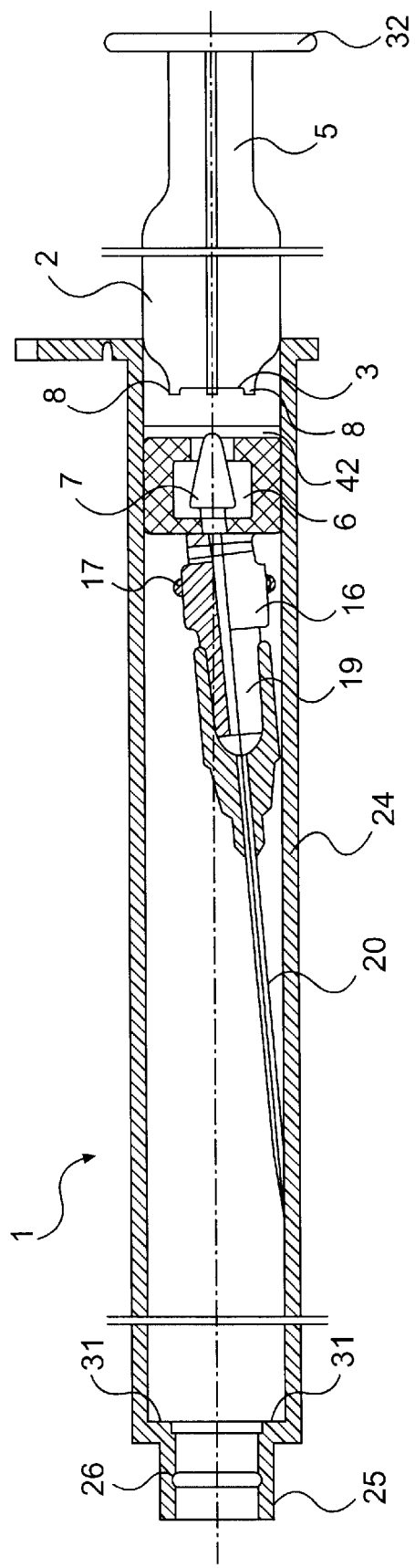
FIG. 4 is a cross sectional side view of a syringe showing how the plunger can be broken, after use, to prevent reuse of the syringe.

As shown in FIG. 4, when the needle 20 is completely pulled into the syringe casing 24, the distal portion 5 of the plunger 2 extends well out of the casing 24. With a small bending moment applied to a side of the distal portion 5, the tines 8 of the weak point 3 break. As shown in FIGS. 4 and 9, when the tines 8 break, the distal portion 5 of the plunger 2 becomes disengaged from the coupling portion 4 of the plunger 2. Without the distal portion 5 attached to the coupling portion 4 of the plunger 2, a user is unable to push the needle 20 back out of the casing 24. If, on the other hand, the user does not break the distal portion 5 and instead tries to push the needle 20 out of the casing 24, the user will be unable to push the needle 20 out of the casing 24 for the reason discussed below.

Figure 3:
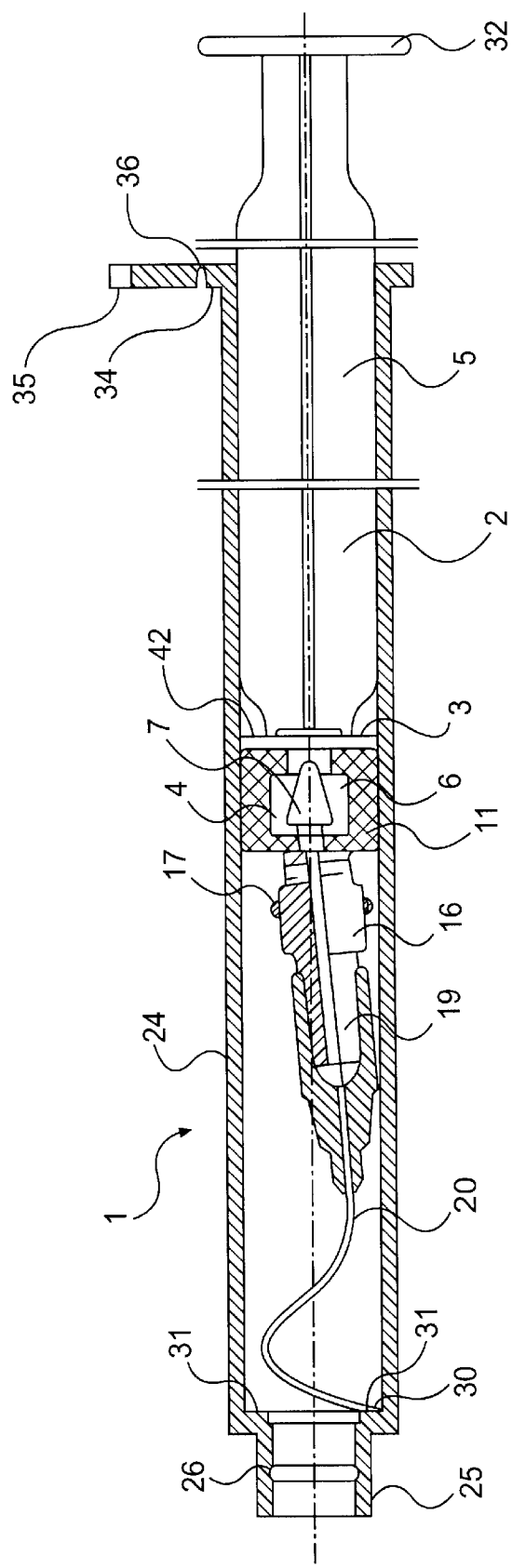
FIG. 3 is a cross sectional side view of a syringe showing the needle destroyed where a user tried to reuse the syringe.

As shown in FIG. 2, when the needle holder 16 is drawn into the casing 24 (after complete activation) and the skin contact end 30 of the needle 20 clears the bore 18 of the cylinder 25, the skin contact end 30 of the needle 20 is forced toward the inner surface of the casing 24. The needle 20 is tipped toward the inner surface of the casing 24 because the arrowhead 7 and hooks 6 are engaged at an angle of approximately 5 degrees; the angular orientation is caused by the inclined base of the arrowhead 7 as previously described. In this fashion, the axis defined by the needle 20 (when completely within the casing 24) is not parallel to the axis upon which the plunger 2 is pulled by the user. As shown in FIG. 3, if a user tries to push the needle 20 back out of the casing 24, the skin contact end 30 of the needle 20 does not pass through bore 18 but rather contacts a wall 31 of the casing which extends circumferentially from the outer surface of the casing 24 toward the cylinder 25. Due to the contact between the skin contact end 30 of the needle 20 and the wall 31, the needle is unable to exit the casing 24. Moreover, if the user continuously increases the force applied to the plunger 2, the needle will collapse.

Although the aforementioned described a preferred embodiment of the invention, the invention is not so restricted. The foregoing description is for exemplary purposes only and is not intended to be limiting. Accordingly, alternatives which would be obvious to one of ordinary skill in the art upon reading the teachings herein disclosed, are hereby within the scope of this invention. The invention is limited only as defined in the following claims and equivalents thereof.

We claim:

1. A safety syringe comprising:
    a syringe barrel;
    a needle holder sealingly installed onto a front end of the syringe barrel, the needle holder having an arrowhead at a rear portion thereof;
    a needle sleeved onto the needle holder;
    a plunger having an coupling portion dimensioned to engage the arrowhead, the plunger moveable between an extended position and an compressed position at which an injection is completed; and
    a cylindrical rubber stopper, having a membrane at one end and a bore at the other end, is coupled to the plunger;
   wherein the rubber stopper and the plunger are sequentially installed into the syringe barrel, wherein the arrowhead has a circumferential groove disposed at a base of the arrowhead, wherein the rubber stopper is hollow and sleeved over the coupling portion, wherein the membrane end of the rubber stopper faces the arrowhead, wherein at the completion of the injection, the arrowhead pierces the membrane and engages the coupling portion, and wherein when the plunger is drawn backwards towards the extended position after the engagement of the arrowhead and the plunger coupling portion, the needle holder and the needle are drawn into the syringe barrel.

2. The syringe according to claim 1, further comprising:
    an inner sealing channel on an internal side of the front end of the syringe barrel; and
    a sealing ring sleeved onto the needle holder and dimensioned to match the inner sealing channel,
   wherein a rear portion of the inner sealing channel has a smaller arc than an arc of the sealing ring, wherein a frontal portion of the inner sealing channel has an inclined face having an arc larger than the arc of the rear portion, wherein the needle holder is slideably engaged in the front end of the syringe barrel by means of the sealing ring, and wherein the needle holder can move in the direction of the syringe barrel when the plunger is withdrawn after engagement of the arrowhead and coupling portion.

3. The syringe according to claim 1, wherein a plane forming the base of the arrowhead is not perpendicular to a central axis of the syringe barrel, wherein after the needle is drawn into the syringe barrel, an axis of the needle is directed toward an inner wall of the syringe barrel, and wherein a subsequent re-compression of the plunger toward the compressed position causes the needle to abut the inner wall of the syringe barrel.

4. The syringe according to claim 1, wherein said plunger comprises a weak portion and a resistance plate fixedly connected to the coupling portion, wherein said plunger has a "+" shape comprised of a vertical rib plate and a horizontal cross rib plate, wherein the vertical rib plate is weakly connected to the resistance plate by means of a plurality of tines, and wherein after completion of the injection and after the needle holder and needle are drawn into the syringe barrel, the weak portion can be broken upon application of a bending moment.

5. The syringe according to claim 4, further comprising:
    a safety mechanism having a wing plate, a check plate, and a flexible film connecting the wing plate and the check plate,
    wherein the safety mechanism is positioned on an exterior surface of the syringe barrel at a position proximate to an insertion bore into which the plunger is inserted, wherein one rib of said vertical rib plate has a groove, wherein the check plate has a groove, wherein the groove of the check plate and the groove of the vertical rib plate may be engaged if the check plate is rotated toward the vertical rib plate by means of the flexible film, and wherein if the groove of the check plate and the groove of the vertical rib plate are engaged, premature completion of the injection is prevented.

6. A safety syringe comprising:
a syringe casing having a distal end and a proximal end;
a plunger channeled in the syringe casing and moveable from an extended position to a compressed position, wherein the plunger has a weak portion, a distal portion, and a coupling portion comprising a plurality of hooks;
a stopper having a membrane, wherein the stopper is affixed to the coupling portion of the plunger, and wherein the membrane is between the proximal end of the syringe casing and the plunger;
a needle holder initially coupled to the proximal end of the syringe casing;
a distally facing arrowhead attached to a distal end of the needle holder;
a proximally facing needle attached to a proximal end of the needle holder, wherein when the plunger is moved from the extended position to the compressed position, the arrowhead punctures the membrane and lockingly engages each of the hooks of the coupling portion of the plunger, and wherein when the plunger is returned to the extended position after engagement of the arrowhead and coupling portion, the needle holder and needle are drawn into an interior of the syringe casing.

7. The syringe according to claim 6, further comprising:
a plurality of o-rings formed on an outer surface of the stopper, wherein the plurality of o-rings frictionally engage an inner surface of the syringe casing when the plunger is moved between the extended position and the compressed position.

8. The syringe according to claim 6, wherein the proximal end of the syringe casing comprises a cylindrical neck portion which houses the needle holder.

9. The syringe according to claim 6, wherein the weak part of the plunger includes a plurality of tines.

10. The syringe according to claim 9, wherein when the plunger is returned to the extended position from the compressed position, the distal portion of the plunger may be disengaged from the weak portion by breaking the tines.

11. A safety syringe comprising:
a syringe casing having a distal end and a proximal end;
a plunger channeled in the syringe casing and moveable from an extended position to a compressed position, wherein the plunger has a weak portion, a distal portion, and a coupling portion;
a stopper having a membrane, wherein the stopper is affixed to the coupling portion of the plunger, and wherein the membrane is between the proximal end of the syringe casing and the plunger;
a needle holder initially coupled to the proximal end of the syringe casing;
a distally facing arrowhead attached to a distal end of the needle holder; and
a proximally facing needle attached to a proximal end of the needle holder, wherein when the plunger is moved from the extended position to the compressed position, the arrowhead punctures the membrane and lockingly engages the coupling portion of the plunger, wherein when the plunger is returned to the extended position after engagement of the arrowhead and coupling portion, the needle holder and needle are drawn into an interior of the syringe casing, wherein the proximal end of the syringe casing comprises a cylindrical neck portion which houses the needle holder, wherein the cylindrical neck portion comprises a circumferential channel formed on an inner surface thereof, and wherein the needle holder comprises a circumferential o-ring on an outer surface thereof which is sized to substantially fill the channel.

12. The syringe according to claim 11, further comprising:
a plurality of o-rings formed on an outer surface of the stopper, wherein the plurality of o-rings formed on the outer surface of the stopper frictionally engage an inner surface of the syringe casing when the plunger is moved between the extended position and the compressed position.

13. The syringe according to claim 11, wherein the stopper substantially covers the coupling portion of the plunger when the plunger is in the extended position, and wherein the stopper substantially covers the arrowhead and the coupling portion when the plunger is in the compressed position.

14. The syringe according to claim 11, wherein the needle has a longitudinal axis, wherein the syringe casing has a longitudinal axis, wherein before engagement of the arrowhead and the coupling portion, the needle axis and the syringe casing axis are substantially parallel, and wherein after engagement of the arrowhead and the coupling portion and after the needle holder and the needle are drawn into the interior of the syringe casing, a mechanism alters the orientation of the needle axis with respect to the syringe axis so that they are not substantially parallel.

15. The syringe according to claim 14, wherein the proximal end of the syringe casing comprises a cylindrical neck portion which houses the needle holder, wherein a circumferential wall extends from an interior end of the cylindrical neck portion to an outer surface of the proximal end of syringe casing, and wherein the needle will contact the wall if the plunger is moved toward the compressed position.

16. A safety syringe comprising:
a syringe casing having a distal end and a proximal end;
a plunger channeled in the syringe casing and moveable from an extended position to a compressed position, wherein the plunger has a weak portion, a distal portion, and a coupling portion;
a stopper having a membrane, wherein the stopper is affixed to the coupling portion of the plunger, and wherein the membrane is between the proximal end of the syringe casing and the plunger;
a needle holder initially coupled to the proximal end of the syringe casing;
a distally facing arrowhead attached to a distal end of the needle holder;
a proximally facing needle attached to a proximal end of the needle holder;
a safety mechanism comprising a check plate affixed to an outer surface of the syringe casing, the check plate adapted to move from an unlocked position to a locked position; and
a notch in a side of the distal portion of the plunger, wherein when the plunger is moved from the extended position to the compressed position, the arrowhead punctures the membrane and lockingly engages the coupling portion of the plunger, wherein when the plunger is returned to the extended position after engagement of the arrowhead and coupling portion, the needle holder and needle are drawn into an interior of the syringe casing, and wherein when the check plate is in the locked position, it engages the notch thereby preventing the plunger from moving from the extended position to the compressed position.

17. A method of preventing reuse of a syringe including a syringe casing having a longitudinal axis, a distal end, and a proximal end having a cylindrical neck portion, a circumferential wall extending from an interior end of the cylindrical neck portion to an outer surface of the proximal end of syringe casing; a plunger having a weak portion, a distal portion, and a coupling portion comprising a plurality of hooks, wherein the plunger is channeled in the syringe casing and is moveable from an extended position to a compressed position; a stopper having a membrane, wherein the stopper is affixed to the coupling portion of the plunger, and wherein the membrane is between the proximal end of the syringe casing and the plunger; a needle holder housed in the cylindrical neck portion of the syringe casing; a distally facing arrowhead attached to a distal end of the needle holder; a proximally facing needle attached to a proximal end of the needle holder and having a needle axis and a needle tip, the method comprising the steps of:

moving the plunger from the extended position to the compressed position; puncturing the membrane with the arrowhead when the plunger is in the compressed position;

coupling the arrowhead to each of the hooks of the coupling portion;

returning the plunger to the extended position and thereby drawing the needle holder and the needle into an interior of the syringe casing; and preventing needle reuse by performing a step selected from the group consisting of:

altering the orientation of the needle axis with respect to the syringe casing axis from an orientation in which the axes are substantially parallel to an orientation in which the needle tip will encounter the circumferential wall if the plunger is moved back toward the compressed position; and disengaging the distal portion of the plunger from the weak part.

18. The method according to claim 17, further comprising the step of:

bending the needle when the needle tip encounters the circumferential wall and when the plunger is moved toward the compressed position after the step of altering the orientation of the needle axis with respect to the syringe casing axis.

19. The method according to claim 17, wherein the weak part of the plunger includes a plurality of tines, and wherein the step of disengaging the distal portion of the plunger from the weak part comprises breaking the tines.

* * * * *